United States Patent
Shirahase et al.

[11] Patent Number: 6,149,923
[45] Date of Patent: Nov. 21, 2000

[54] ANTIRHEUMATIC AGENT

[75] Inventors: Hiroaki Shirahase, Nagaokakyo; Akihisa Yoshimi, Takatsuki; Fumio Fukata, Osaka; Hideki Okunishi; Yuta Kobayashi, both of Izumo, all of Japan

[73] Assignee: Kyoto Pharmaceutical Industries, Ltd., Kyoto, Japan

[21] Appl. No.: 09/202,368

[22] PCT Filed: Jun. 6, 1997

[86] PCT No.: PCT/JP97/01974

§ 371 Date: Dec. 10, 1998

§ 102(e) Date: Dec. 10, 1998

[87] PCT Pub. No.: WO97/47297

PCT Pub. Date: Dec. 18, 1997

[30]     Foreign Application Priority Data

Jun. 11, 1996   [JP]   Japan ................................. 8-149549

[51] Int. Cl.[7] .......................... A61K 9/00; A61K 31/35; A01N 43/16
[52] U.S. Cl. .......................... 424/400; 514/825; 514/456
[58] Field of Search ............... 424/400; 514/825, 514/456

[56]            References Cited

U.S. PATENT DOCUMENTS

| | | | |
|---|---|---|---|
| 4,066,756 | 1/1978 | Orr et al. ................................. | 514/161 |
| 4,847,286 | 7/1989 | Tamaki et al. .......................... | 514/456 |

OTHER PUBLICATIONS

Yoshimi et al Importance of Hydrolysis of Amino Acid Moiety in Water–Soluble Prodrugs of Disodium Cromoglycate for Increased Oral Bioavailability 1992 J. Pharmacobio–Dyn 15:339–345.

Mori et al Pro–drugs for the Oral Deliver of Disodium Cromoglycate 1988 Chem. Pharm. Bull. 36:338–344.

Primary Examiner—Thurman K. Page
Assistant Examiner—Todd D. Ware
Attorney, Agent, or Firm—Leydig, Voit & Mayer, Ltd.

[57]       ABSTRACT

An antirheumatic agent comprising diethyl L-lysylcromoglycate of the following formula

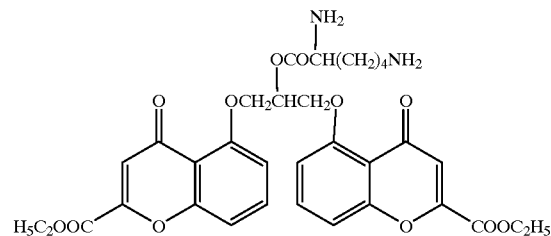

or a nontoxic salt thereof as an active ingredient. This compound has an anti-inflammatory action and immunomodulating action, is absorbed by oral administration to be delivered efficiently to local sites, and is associated with fewer side effects, so that it serves well as an antirheumatic agent that can be administered orally.

6 Claims, No Drawings

ANTIRHEUMATIC AGENT

This application is a 371 of PCT/JP97/01974, filed Jun. 6, 1997.

TECHNICAL FIELD

The present invention relates to an antirheumatic agent comprising diethyl L-lysylcromoglycate or a nontoxic salt thereof as an active ingredient.

BACKGROUND ART

A typical rheumatic disease—chronic rheumatoid arthritis (hereinafter RA)—is a systemic connective-tissue disease having a main symptom of polyarthritis chronica, and is one of the autoimmune diseases. The disease type thereof is generally polyarthritis which is progressive and chronic. It includes various clinical types such as one showing spontaneous remission, one showing highly progressive destruction and absorption of joints (e.g., arthritis dissecans) and the like. Clinical symptoms thereof include arthritis, swelling of joint, pain, deformation, morning stiffness, rheumatoid nodule, angiitis and the like.

For internal therapy of RA at present, nonsteroidal antiflammatory agents (e.g., aspirin, indometacin, diclofenac sodium, ibuprofen, loxoprofen sodium, piroxicam, ampiroxicam, naproxen, and the like), adrenocorticosteroidal agents (e.g., intraarticular injection and oral administration of prednisolone, and the like), immunomodulators (e.g., gold preparation, D-penicillamine, bucillamine, actarit and the like), immunosuppressive agents (e.g., methotrexate, mizoribine and the like), and the like are used. These medicaments, nevertheless, fail to provide sufficient therapeutic effects, but rather, cause various side effects. For example, nonsteroidal antiinflammatory agents may cause peptic ulcer, nephropathy, hepatopathy and the like, adrenocorticosteroidal agents may induce and exacerbate infectious diseases, diabetes, moon face, peptic ulcer, adrenocortical insufficiency, thrombophlebitis, osteoporosis and the like, immunomodulators may cause dermatopathy, nephropathy, stomatitis and the like, and immunosuppressive agents may cause hepatopathy, leukopenia, thrombocytopenia and the like, some of which constituting severe side effects.

In view of the above-mentioned situation, there is a demand for the development of an antirheumatic agent effective for the alleviation and suppression of the symptoms of RA and causing fewer side effects.

It is therefore an object of the present invention to provide an antirheumatic agent that is delivered to local sites after oral administration, that is effective for the treatment of RA and that causes fewer side effects.

DISCLOSURE OF THE INVENTION

The present inventors have conducted various studies to solve the above-mentioned problems and found that cromoglycic acid derivatives of the following formula (I):

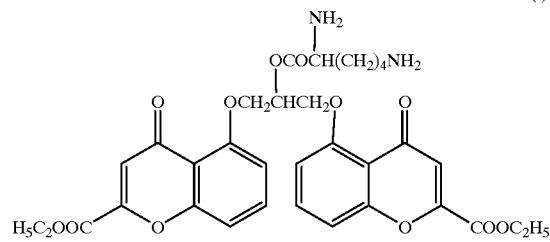

namely, diethyl L-lysylcromoglycate and a nontoxic salt thereof, are efficiently absorbed from the digestive tract, delivered to local sites and suppress the symptoms of polyarthritis, which is the main symptom of RA, and developed further studies to result in the completion of the present invention.

That is, the present invention provides the following.

(1) An antirheumatic agent comprising diethyl L-lysylcromoglycate or a nontoxic salt thereof as an active ingredient.

(2) The antirheumatic agent of (1) above, which is an oral preparation.

(3) The antirheumatic agent of (1) or (2) above, further comprising an organic acid.

(4) The antirheumatic agent of (3) above, wherein the organic acid is at least one organic carboxylic acid selected from the group consisting of maleic acid, fumaric acid, tartaric acid, citric acid, succinic acid, malic acid, oxalic acid, mandelic acid, malonic acid and benzoic acid.

(5) A pharmaceutical composition for the therapy of rheumatism, comprising diethyl L-lysylcromoglycate or a nontoxic salt thereof, and a pharmaceutically acceptable carrier.

(6) The pharmaceutical composition for the therapy of rheumatism according to (5) above, which is an oral preparation.

(7) The pharmaceutical composition for the therapy of rheumatism according to (5) or (6) above, further comprising an organic acid.

(8) The pharmaceutical composition for the therapy of rheumatism according to (7) above, wherein the organic acid is at least one organic carboxylic acid selected from the group consisting of maleic acid, fumaric acid, tartaric acid, citric acid, succinic acid, malic acid, oxalic acid, mandelic acid, malonic acid and benzoic acid.

(9) A method for the therapy of rheumatism comprising administering an effective amount of diethyl L-lysylcromoglycate or a nontoxic salt thereof to a patient.

(10) A use of diethyl L-lysylcromoglycate or a nontoxic salt thereof for the therapy of rheumatism.

(11) A use of diethyl L-lysylcromoglycate or a nontoxic salt thereof for the production of a pharmaceutical agent for the therapy of rheumatism.

(12) A commercial package comprising the pharmaceutical composition for the therapy of rheumatism of any of (5)–(8) above and a written matter associated therewith, the written matter stating that said pharmaceutical composition can or should be used for the therapy of rheumatism.

In the present invention, diethyl L-lysylcromoglycate may be converted to a nontoxic salt, particularly an acid addition salt thereof to be mentioned later, to increase absorption efficiency, stabilize diethyl L-lysylcromoglycate and facilitate isolation and production of an oral preparation.

In the present invention, moreover, oral administration of diethyl L-lysylcromoglycate in the presence of an organic acid leads to strikingly increased solubility of diethyl L-lysylcromoglycate in the digestive tract. Therefore, addition of an organic acid to be mentioned later to the antirheumatic agent of the present invention is desirable.

Diethyl L-lysylcromoglycate is a known compound and can be produced by a method known per se. For example, diethyl cromoglycate and L-lysine are reacted to produce this compound.

L-Lysine is subjected to the present reaction as a free carboxylic acid or a reactive derivative thereof.

Diethyl L-lysylcromoglycate preferably forms a nontoxic salt (acid addition salt) at its amino acid residue. An acid to form such nontoxic salt is free of any particular limitation as long as it can form a salt with the amino acid residue moiety and it is pharmaceutically acceptable. For example, mineral acids such as hydrochloric acid, sulfuric acid, phosphoric acid and nitric acid; and organic acids such as oxalic acid, fumaric acid, maleic acid, citric acid, tartaric acid, methanesulfonic acid and toluenesulfonic acid are exemplified. By converting to such salts, absorption from the digestive tract can be improved and production of the preparation can be facilitated.

Diethyl L-lysylcromoglycate or a nontoxic salt thereof thus produced is diluted with a pharmaceutical excipient by a known method to give an antirheumatic agent, particularly an oral antirheumatic agent. The dilution is performed by a known method such as mixing and the like. Examples of the excipient include starch, lactose, sugar, calcium carbonate, calcium phosphate, and the like.

For a higher solubility of said antirheumatic agent in the digestive tract, higher absorption in blood and efficient delivery to lesion, said antirheumatic agent preferably contains an organic acid. The organic acid is free of any particular limitation as long as it is pharmaceutically acceptable, and is exemplified by organic carboxylic acids such as maleic acid, fumaric acid, tartaric acid, citric acid, succinic acid, malic acid, oxalic acid, mandelic acid, malonic acid and benzoic acid. The organic acid is added in a proportion of 0.05–6 moles, preferably 0.05–3 moles, per mole of diethyl L-lysylcromoglycate.

This antirheumatic agent may contain other additives on demand. For example, binders (e.g., starch, gum arabic, carboxymethylcellulose, hydroxypropylcellulose, crystalline cellulose and the like), lubricants (e.g., magnesium stearate, talc and the like), disintegrators (e.g., calcium carboxymethylcellulose, talc and the like) may be used as preferable additives. After addition of various ingredients, the mixture is formulated in a dosage form suitable for oral administration, such as capsule, tablet, subtilized granules, granules, dry syrup and the like, according to a known method.

Diethyl L-lysylcromoglycate and a nontoxic salt thereof to be used in the present invention are effective for the suppression of symptoms of RA and permit high absorption thereof from the digestive tract and delivery to local sites, so that they are used as oral antirheumatic agents.

For oral administration of said therapeutic agents, a daily dose is preferably administered orally in one to three doses. While the dose varies depending on the condition, age, body weight and the like of patients, 20–1000 mg of the active ingredient—diethyl L-lysylcromoglycate or a nontoxic salt thereof—is administered to an adult daily in one to three doses.

EXAMPLES

The present invention is explained in more detail in the following by way of example and experimental example, to which the present invention is not limited.

Example 1

Synthesis of diethyl L-lysylcromoglycate dihydrochloride (1) Diethyl cromoglycate (524 mg), di-t-butoxycarbonyl-L-lysine (520 mg) and dimethylaminopyridine (61 mg) are added to methylene chloride (10 ml). N,N-Dicyclohexylcarbodiimide (310 mg) is added at 0° C., and the mixture is stirred at the same temperature for 30 minutes and at room temperature for 6 hours. The precipitated urea compound is filtered off and the filtrate is concentrated and purified by silica gel column chromatography to give di-t-butoxycarbonyl-diethyl L-lysylcromoglycate (580 mg, yield 68%).

IR (KBr, cm$^{-1}$) 1740, 1710, 1690, 1655

NMR (CDCl$_3$, δppm)

1.41 (18H, s, ——C(CH$_3$)$_3$, 1.41 (6H, t, J = 7Hz, ——CH$_2$CH$_3$), 1.4–2.1 (6H, m, ——(CH$_2$)$_3$——), 2.8–3.3 (2H, m, ——CH$_2$NH——), 3.9–4.4 (1H, m, ——CHNH——), 4.43 (4H, q, J = 7Hz,

——CH$_2$CH$_3$), 4.3–4.8 (4H, m,——CH$_2$CHCH$_2$——), 4.7–5.5 (2H, m, ——NH——), 5.4–5.9 (1H, m,

——CH$_2$CHCH$_2$), 6.87 (2H, s, chromone 3-position ——H), 6.8–7.4 (4H, m, chromone 6- position, 8-position ——H), 7.58 (2H, t, J = 9Hz, chromone 7-position ——H)

(2) The compound (470 mg) obtained in (1) is dissolved in formic acid (1.1 ml), and a solution (2.8 ml) of 1.4M hydrogen chloride in dioxane is added under ice-cooling. The mixture is stirred at room temperature for 30 minutes. The reaction mixture is poured into isopropyl ether, and the precipitate is collected by filtration to give diethyl L-lysylcromoglycate dihydrochloride (351 mg, yield 88%).

IR (KBr, cm$^{-1}$) 1740

NMR (DMSO-d$_6$, δppm)

1.34 (6H, t, J = 7Hz, ——CH$_2$CH$_3$), 1.4–2.2 (6H, m, ——(CH$_2$)$_3$——), 2.3–3.0 (2H, m,

——CH$_2$NH$_3^+$), 3.7–4.2 (1H, m, ——CHNH$_3^+$), 4.36 (4H, q, J = 7Hz, ——CH$_2$CH$_3$), 4.3–4.9 (4H,

Experimental Example 1

Suppression of collagen-induced arthritis by diethyl L-lysylcromoglycate dihydrochloride in mice.

According to the method of Courtenay et al. (Courtenay, J. S. et al.: Immunization against heterologous type II collagen induces arthritis in mice. Nature, 283:666, 1980), male DBA/ 1J mice (Charles River) were sensitized with bovine type II collagen to induce collagen-induced arthritis (rheumatoid arthritis). After the onset of arthritis, diethyl L-lysylcromoglycate dihydrochloride was orally administered and its suppressive effect was examined. The method is detailed in the following.

Male DBA/1J mice (8-week-old) were pre-bred for one week and divided into the following 4 groups based on body weight.
(1) Normal group 10 mice
(2) Control group 10 mice
(3) Treated group L 10 mice
(4) Treated group H 10 mice Bovine type II collagen (2 mg) was dissolved in 0.01M acetic acid (1 ml) and suspended in an equivalent amount of Freund's complete adjuvant, and 0.1 ml thereof was interademmally injected to the control group, treated group L and treated group H at 9 weeks of age at the base of the tail, followed by the second injection three weeks later at 12 weeks of age.

Starting from day 31 after the first injection of collagen till the end of the treatment, the mice of each group were scored (arthritis score) for the levels of redness, swelling and stiffness of four limbs by a blind test method twice a week The scores were taken according to a method similar to a method of Bjoerk et al. (Bjoerk, J. and KIeinau, S.: Pamdoxcal effects of LS-26 16 (Linomide) treatment in the type 11 collagen arthritis model in mice, Agents and Actions, 27:319–321, 1989.), wherein normal was rated 0 point, inflammation on one digit was 1 point, inflammation on two or more digits and normal metacarpal region and metacarpal region of the limbs, or inflammation on one digit and metacarpal region and metatarsal region of the limbs was 2 points, and inflammation on digits and metacarpal region and metatarsal region of the limbs was 3 points, each mouse scoring 0 to 12 points in total.

At day 38 from the initial injection of collagen, the onset of arthritis was found in the control group, treated group L and treated group H. The arthritis score did not vary between groups.

The treatment was continued for 6 weeks from day 41 from the initial injection. To be specific, diethyl L-lysylcromoglycate dihydrochloride was dissolved in distilled water and forcibly administered orally to the mice of the treated group L at a dose of 30 mg/kg/day and treated group H at a dose of 100 mg/kg/day, once a day for 6 weeks. Distilled water was given to the control group in the same manner.

The arthritis scores at 3 days before the initiation of treatment and day 38 after the initiation of treatment are shown in the following Table 1. Comparative testing by U-test with control group showed a significant improvement in the arthritis scores of the treated group H.

TABLE 1

| | arthritis score | |
|---|---|---|
| | Day 38 after initial collagen injection (3 days before initiation of treatment) | Day 79 after initial collagen injection (38 days after initiation of treatment) |
| Normal group | 0.000 ± 0.000 | 0.000 ± 0.000** |
| Control group | 1.600 ± 0.452 | 10.600 ± 0.476 |
| Treated group L (30 mg/kg/day) | 1.800 ± 0.512 | 8.900 ± 1.242 |
| Treated group H (100 mg/kg/day) | 2.000 ± 0.650 | 6.444 ± 1.260** |

Each value is mean ± standard error (n = 9–10)
**$p < 0.01$ (U-test relative to control group)

At day 42 after the initiation of treatment, blood was taken from carotid artery and the mice were exsanguinated to death under ether anesthesia The anti-type II collagen antibody titer in blood was determined by ELISA according to the method of Stuart et al. (Stuart, J. M. et al.: Nature and specificity of the immune response to collagen in type II collagen-induced arthritis in mice, J. Clin. Invest., 69:673–683, 1982). The results are shown in the following Table 2. Comparative testing by ANOVA method with the control group revealed a significant decrease in anti-type II collagen antibody titer in blood in the treated group L and treated group H.

TABLE 2

| anti-bovine type II collagen antibody titer in blood | |
|---|---|
| | Day 83 after initial collagen injection (42 days after initiation of treatment) |
| Normal group | 0.000 ± 0.000** |
| Control group | 0.303 ± 0.006 |
| Treated group L (30 mg/kg/day) | 0.248 ± 0.013** |
| Treated group H (100 mg/kg/day) | 0.214 ± 0.011** |

Each value is mean ± standard error (n = 9–10).
**$p < 0.01$ (ANOVA method relative to control group)

In addition, the whole body was X-ray photographed and destruction state of the bone of feet and digits of the four limbs was scored (X-ray score) by a blind test according to the criteria of Gliman et al. (Gliman S. C. et al.: Immunological abnormalities in rats with adjuvant-induced arthritis, II. Effect of antiarthritic therapy on immune function in relation to disease development, Int. J. Immunopharmacol., 9:9–16, 1987), wherein normal was rated 0 point, destruction in one joint was 1 point, destruction in two or more joints, though not all joints, was 2 points, and destruction in all joints was 3 points, each mouse scoring 0 to 12 points in total. The results are shown in the following Table 3. Comparative testing by U-test with the control group revealed a significant improvement in X-ray score in the treated group H.

TABLE 3

|  | X-ray score |
| --- | --- |
|  | Day 83 after initial collagen injection (42 days after initiation of treatment) |
| Normal group | 0.000 ± 0.000** |
| Control group | 10.400 ± 0.400 |
| Treated group L (30 mg/kg/day) | 9.020 ± 0.700 |
| Treated group H (100 mg/kg/day) | 5.900 ± 1.100** |

Each value is mean ± standard error (n = 9–10).
**$p < 0.01$ (U-test relative to control group)

The collagen-induced arthritis in the mice used in this experiment is one of the test models of autoimmune arthritis most similar to human RA.

The administration of diethyl L-lysylcromoglycate resulted in the suppression of the symptoms of collagen-induced arthritis (rheumatoid arthritis) and suppression of bone destruction of feet and digits of the four limbs as evidenced in X-ray photographs. Therefrom it follows that said compound has anti-inflammatory action and antirheumatic action. Moreover, the suppression of an increase in the anti-collagen antibody titer in blood indicated some immunomodulating action of said compound.

From the above results, it has been clarified that diethyl L-lysylcromoglycate has anti-inflammatory action and immunomodulating action, so that it provides an antirheumatic agent effective for rheumatoid arthritis.

The formulation examples are given in the following.

Formulation Example 1

The tablets having the following formulation can be produced by a conventional method.

| Compound of Example 1 | 5 mg |
| --- | --- |
| Polyvinyl pyrrolidone | 20 mg |
| Starch | 75 mg |
| Magnesium stearate | 2 mg |

Formulation Example 2

The tablets having the following formulation can be produced by a conventional method.

| Compound of Example 1 | 10 mg |
| --- | --- |
| Tartaric acid | 50 mg |
| Starch | 50 mg |
| Magnesium stearate | 3 mg |

Industrial Applicability

The diethyl L-lysylcromoglycate and a nontoxic salt thereof to be used in the present invention are rapidly absorbed from the digestive tract after oral administration and delivered efficiently to blood system and local sites to exhibit efficacy. Said compounds are effective for the suppression of the symptoms of rheumatoid arthritis and associated with fewer side effects as compared to conventional antirheumatic agents. Hence, said compounds are highly safer than the conventional antirheumatic agents and can be used as antirheumatic agents that can be administered orally.

This application is based on application No. 149549/1996 filed in Japan, the content of which is incorporated hereinto by reference.

What is claimed is:

1. A method of treating rheumatism, comprising administering an effective amount of diethyl L-lysylcromoglycate or a nontoxic salt thereof to a patient.

2. A method of treating rheumatism, comprising administering a pharmaceutical composition to a patient, wherein the pharmaceutical composition comprises diethyl L-lysylcromoglycate or a nontoxic salt thereof and a pharmaceutically acceptable carrier.

3. The method of claim 1, wherein the diethyl L-lysylcromoglycate or the nontoxic salt thereof is administered orally.

4. The method of claim 2, wherein the pharmaceutical composition is administered orally.

5. The method of claim 2, wherein the pharmaceutical composition further comprises an organic acid.

6. The method of claim 5, wherein the organic acid is at least one organic carboxylic acid selected from the group consisting of maleic acid, fumaric acid, tartaric acid, citric acid, succinic acid, malic acid, oxalic acid, mandelic acid, malonic acid, and benzoic acid.

* * * * *